(12) United States Patent
Shukla

(10) Patent No.: US 8,431,167 B2
(45) Date of Patent: Apr. 30, 2013

(54) PLANT EXTRACTS COMPOSITION FOR THE TREATMENT OF LIVER DYSFUNCTION-JAUNDICE

(76) Inventor: Mukesh Harilal Shukla, Surendranagar (IN)

(*) Notice: Subject to any disclaimer, the term of this patent is extended or adjusted under 35 U.S.C. 154(b) by 0 days.

(21) Appl. No.: 13/243,859

(22) Filed: Sep. 23, 2011

(65) Prior Publication Data

US 2012/0015061 A1 Jan. 19, 2012

(30) Foreign Application Priority Data

Jan. 19, 2011 (IN) .......................... 153/MUM/2011

(51) Int. Cl.
*A61K 36/00* (2006.01)
*A61K 36/906* (2006.01)

(52) U.S. Cl.
USPC .......................................... 424/756; 424/725

(58) Field of Classification Search ........................ None
See application file for complete search history.

(56) References Cited

PUBLICATIONS

Kumar et al, Free and bound phenolic antioxidants in amla (*Emblica officinalis*) and turmeric (*Curcuma longa*). International Network of Food Data Systems, Aug. 2006 vol. 19, issue 5 p. 446-452.*
Rawal et al, In vitro antioxidant activity of *Gymnosporia montana* leaves. Indian Drugs, (Oct. 2009) vol. 46, No. 10, pp. 40-43.*

* cited by examiner

*Primary Examiner* — Qiuwen Mi
(74) *Attorney, Agent, or Firm* — Hultquist, PLLC; David Bradin

(57) ABSTRACT

Plant extracts compositions comprising extracts of *Curcuma longa*, *Phyllanthus emblica* and *Gymnosporea montana* and at least a carrier. The extracts used to prepare the composition are prepared from specific parts of the respective plants like extract of *Curcuma longa*; *Phyllanthus emblica* and *Gymnosporea montana* are prepared from tubers, fruits and leafs of respective plants. The compositions can be used to treat liver dysfunction.

9 Claims, No Drawings

PLANT EXTRACTS COMPOSITION FOR THE TREATMENT OF LIVER DYSFUNCTION-JAUNDICE

FIELD OF THE INVENTION

The present invention relates to the plant extract composition for the treatment of liver dysfunction—Jaundice. Further the invention relates to plant extracts composition, comprising extract of *Curcuma longa, Phyllanthus emblica* and *Gymnosporea montana* and at least a carrier. The present invention also relates to process for preparing the extract composition.

This application claims priority of Indian Patent Application No. 153/MUM/2011, filed on Jan. 19, 2011. The disclosure of such application is hereby incorporated herein by reference in its entirety, for all purposes.

BACKGROUND OF THE INVENTION

The liver of our body is an organ which acts like a filter: it helps digest food by filtering out bad chemicals and substance from the food we eat. It is an energetic and critical part of our digestive system, and one of the most important organs in our body. However, the liver is also prone to damage. There are many causes of damage to liver, from chemical to disease.

At presently near about two million Americans suffer from liver damage caused by alcohol abuse. About 10 to 20 percent of large alcohol takers will develop cirrhosis of the liver, which is characterized by scarring of the liver and causes irreversible damage. If large alcohol takers do not stop drinking, cirrhosis can cause poor health and, ultimately, death. In addition to cirrhosis, heavy drinkers may suffer from chronic liver disease or alcoholic hepatitis.

Damage to the liver can lead to problems with blood sugar levels. When alcohol is present in the body, the liver works to metabolize it. Because the liver is busy metabolizing alcohol, it is often not able to adequately maintain blood sugar levels, which may result in hypoglycemia (low levels of blood sugar). Hypoglycemia is most likely to occur in individuals who have not maintained an adequate diet. When it occurs, the brain is not able to receive the energy it needs to function, and symptoms such as hunger, weakness, headache, tremor, and even coma (in severe cases) may occur.

Hepatic insufficiency can be defined as a clinical condition resulting from the additive effects of toxic metabolic defects. It may occur in any form of liver disease. It is usually gradual and relatively asymptomatic (David Cayer, American journal of digestive disease).

Hepatic insufficiency can be characterized by condition where liver is unable to perform its normal function. If the same is not treated then it may lead to impaired function of filtration carried out by liver and as a result, lots of waste products get accumulated in the blood and lead to serious condition of hepatic coma.

Jaundice is a clinical condition which is characterized by yellowing of the skin and the whites of the eyes which is due to an accumulation of a cellular waste production called bilirubin. The discoloration is often, but by no means always, accompanied by itching, which can be intense, as well as by nausea, vomiting, headache, fever, dark-colored urine, abdominal pain, loss of appetite, abdominal swelling, and light-colored stools. Jaundice is not a disease in and of itself, but a sign that the liver is having inability to perform the normal function specifically handling bilirubin. The liver makes bilirubin from dying red blood cells and other sources. It then converts bilirubin into bile, which has several purposes, among them the digestion of fatty acids and neutralization of stomach acid. If there is too much bilirubin production for the liver to deal with, or if the liver's functioning is compromised, jaundice will be the outcome at the end. Jaundice may be caused by several different disease processes. It is helpful to understand the different causes of jaundice by identifying the problems that disrupt the normal bilirubin metabolism and/or excretion.

The liver has many functions. One of the liver's functions is to produce and secrete bile into the intestines to help digest dietary fat. Another is to remove toxic chemicals or waste products from the blood, and bilirubin is a waste product. The liver removes bilirubin from the blood. After the bilirubin has entered the liver cells, the cells conjugate (attaching other chemicals, primarily glucuronic acid) to the bilirubin, and then secrete the bilirubin/glucuronic acid complex into bile. The complex that is secreted in bile is called conjugated bilirubin. The conjugated bilirubin is eliminated in the feces. (Bilirubin is what gives feces its brown color.) Conjugated bilirubin (called direct) is distinguished from the bilirubin that is released from the red blood cells and not yet removed from the blood which is termed unconjugated (called indirect) bilirubin.

Jaundice occurs when there is 1) too much bilirubin being produced for the liver to remove from the blood. (For example, patients with hemolytic anemia have an abnormally rapid rate of destruction of their red blood cells that releases large amounts of bilirubin into the blood), 2) a defect in the liver that prevents bilirubin from being removed from the blood, converted to bilirubin/glucuronic acid (conjugated) or secreted in bile, or 3) blockage of the bile ducts that decreases the flow of bile and bilirubin from the liver into the intestines. (For example, the bile ducts can be blocked by cancers, gallstones, or inflammation of the bile ducts). The decreased conjugation, secretion, or flow of bile that can result in jaundice is referred to as cholestasis: however, cholestasis does not always result in jaundice.

The bile ducts normally discharge pigments and bile salts into the intestine and an obstruction in the ducts can cause jaundice. The yellowish pigmentation of the skin is because of bile mixing with the blood. The obstruction could be caused by gallstones or an inflammation of the liver, known as hepatitis.

Results and statistical analysis of many epidemiological studies, clinical trials, and laboratory mechanistic studies indicate that many medicinal plants may be useful in the prevention and treatment of liver dysfunction and its related diseased conditions.

There are many poly herbal formulations available in the market claiming to be useful for many diseased conditions including liver damage, liver cirrhosis, hepatic insufficiency and many more but majority of such poly herbal formulations doesn't contain the standardized material and appropriate proportion of required plant extract with required active constituents according to targeted condition.

It is visible from the above discussion that there is still exists a long felt need and a strong demand in the society for the herbal formulation based on plant of natural kingdom, which provides beneficial activity against liver dysfunctional the same time doesn't have major side effects to human beings.

We have surprisingly found that when extract of specific parts of specific plant are formulated in to a composition, the said composition exhibits superior activity in the treatment of liver dysfunction with minimal or no side effects at all.

OBJECT OF THE INVENTION

The main object of the present invention is to provide plant extract composition for the treatment of the condition of liver dysfunction. It is another object of the present invention to provide a plant composition which comprises extracts of *Curcuma longa, Phyllanthus emblica* and *Gymnosporea montana* and at least a carrier. It is yet another object of the present invention to provide processing steps of preparing the plant extracts composition.

SUMMARY OF THE INVENTION

The objects as mentioned above are achieved by providing a plant extracts composition comprising extracts of *Curcuma longa, Phyllanthus emblica* and *Gymnosporea montana* and at least a carrier. The extracts used to prepare the composition are prepared from specific parts of the respective plants like extract of *Curcuma longa; Phyllanthus emblica* and *Gymnosporea montana* are prepared from tubers, fruits and leafs of respective plants.

DETAILED DESCRIPTION OF THE INVENTION

The present invention is contemplates plant extract composition exhibiting activity against liver dysfunction wherein the plant extracts composition comprises extracts of *Curcuma longa, Phyllanthus emblica* and *Gymnosporea montana* and at least a carrier.

As used herein, liver dysfunction means the diseases condition known as jaundice and hepatic insufficiency and preferably the disease condition of jaundice.

Active compound responsible for specific activity can be found in higher concentrations in specific parts of medicinal plants and in lower concentration in other parts of the medicinal plant. The specific part of the medicinal plant having the higher concentration of the plant are selected and processed further to use for the preparation of the plant extract composition. Preferably the extracts of the specific part of plant are used for the preparation of the composition of the present invention to provide the desired therapeutic effect in liver dysfunction condition.

*Curcuma longa*

*Curcuma Longa* is a small perennial herb native to India bearing many rhizomes on its root system which are the source of its culinary spice known as Turmeric. Extract of tuber part of *Curcuma* long is used for the preparation of the present invention.

Botanical Classification:
Family: Zingiberaceae
Genus: *Curcuma*
Species: *Longa*

*Phyllanthus emblica*

*Phyllanthus emblica* is small to medium sized deciduous tree, sometimes up to 25 m tall but usually much shorter, up to 7.5 m; trunk often crooked and gnarled, up to 35 cm in diameter; bark thin, smooth, grey, peeling in patches, with numerous knobs. Extract of fruits of *Phyllanthus emblica* is used for the preparation of the present invention.

Botanical Classification:
Family: Euphorbiaceae
Genus: *Phyllanthus*
Species: *Emblica*

*Gymnosporia montana*:

*Gymnosporia montana* is a traditional herbaceous plant of Celastraceous family found in different regions of India. In vernacular language it is called as Vikalo. Extract of leaves of *Gymnosporia montana* is used for the preparation of the present invention.

Botanical Classification:
Family: Celastraceae
Genus: *Gymnosporia*
Species: *Montana*

The extracts of different parts of herbal plant as used herein are in the form of dried powder to facilitate the preparation of present plant extracts composition.

The plant extracts composition of the present invention is able to be administered either orally. The plant extract composition can be selected from the group consisting of tablet, capsule, powder, beads, pellets, granules, solution, syrup, suspension, oleoresin or emulsion. The preferred composition of the present invention is selected from tablet, capsules, powders or granules. More preferably the plant extract composition is in the form of capsules, tablet and syrup.

The plant extract composition of the present invention can be prepared by using any common techniques available in the art.

The plant extract composition of the present invention comprises 10-25% w/w extract of *Curcuma longa*, 10-25% w/w extract of *Phyllanthus emblica* and 50-70% w/w extract *Gymnosporea Montana* and rest is made up by carrier.

The carrier as used here in is selected from group consisting of diluent, binder, disintegrant, glidant and lubricant. There may be one or more carriers are used in the preparation of composition.

Diluents are inert excipients that are used to adjust the bulk in the pharmaceutical composition. Commonly used diluents include but not limited to lactose, dicalcium phosphate, micro crystalline cellulose, kaolin, mannitol and starch. Diluents are to be used in the range of 5 to 90% w/w of composition.

Binders are utilized in the pharmaceutical composition to impart cohesive force to the powder which allows the powder materials to retain its integrity once it is compressed. Commonly used binders include but not limited to carboxymethyl cellulose, methyl cellulose, polyvinylpyrrolidone, ethyl cellulose, pregelatinized starch and gelatin. Binders are to be used in the range of 1 to 10% w/w of composition.

A disintegrant is an excipient, or a mixture of excipients added to facilitate breakup of the binded powdered materials form the composition. Dried and powdered corn starch or potato starch are widely used disintegrants. They have a good affinity towards water and swell when moistened resulting in to rupture of the tablet. A group of materials known as super-disintegrants include croscarmelose, a cross-linked cellulose, crosprovidone, a cross-linked polymer and sodium starch glycolate, a cross-linked starch. Disintegrants are to be used in the range of 2 to 10% w/w of composition.

Lubricants are used in pharmaceutical composition to prevent adhesion of the material to the surface of dyes and punches in case of tablet composition. Commonly used lubricants include but not limited to magnesium stearate, calcium stearate, talc, stearic acid, hydrogenated vegetable oils and PEG. Lubricants are to be used in the range of 0.5 to 4% w/w of composition.

Glidants are used in pharmaceutical composition to improve the flow characteristics of the powder materials. Colloidal silicon dioxide or anhydrous silica is a common glidant. Talc may serve as a combined lubricant/glidant. Glidants are to be used in the range of 0.5 to 4% w/w of composition. The compounds/extracts procured are than also tested for the standard laboratory analytical tests as TLC, Identification, M.P., Assay by Spectrophotometer, Heavy Metals, and Microbial Profile.

The plant extracts composition of the present invention is prepared by the techniques available in the art.

The process to prepare the plant extracts composition of present invention is described below in stepwise manner.

a) sifting the extracts of *Curcuma longa, Phyllanthus emblica* and *Gymnosporea montana* through 20# and at least one carrier through 40# and;
b) mixing of sifted extracts of step a) and optionally;
c) granulating the material of step b) using solvent and optionally;
d) drying of granules of step c) and optionally;
e) sifting dried granules of step d) through 20# and
f) mixing materials of step b) or e) with at least a carrier from step a) and
g) filling of material of step f) in to capsules or compressing in to tablets.

The processing steps during the preparation of the plant extract composition like sifting, granulation, drying, mixing and filling of capsule or tablet compression are to be performed as per the technique available in the art to any ordinary skilled person from this field.

The present invention also provides method of treating sign and symptoms of liver dysfunction, wherein the method comprises administering to a patient in need thereof, the plant extracts composition of the present invention.

EXAMPLES

The invention described here by way of example only, and it is to be recognized that modification thereto falling within the scope and spirit of this specification, and which would be obvious to a person skilled in the art based upon the disclosure herein, are also considered to be included within the scope of the invention.

Example 1

Capsule Composition

| Ingredients | % w/w |
|---|---|
| Extract of *Curcuma longa* | 20 |
| Extract of *Phyllanthus emblica* | 20 |
| Extract of *Gymnosporia montana* | 59 |
| Colloidal silicon dioxide | 1 |
| Total | 100 |

Procedure: Extracts of *Curcuma longa, Phyllanthus embelica, Gymnosporia montana* and colloidal silicon dioxide are shifted through 40#. All the shifted materials are mixed for 5 minutes. The mixed materials are filled in hard gelatin capsule of appropriate size.

Example 2

Tablet Composition

| Ingredients | % w/w |
|---|---|
| Extracts of *Curcuma longa* | 15 |
| Extracts of *Phyllanthus emblica* | 15 |
| Extracts of *Gymnosporia montana* | 55 |
| Lactose anhydrous | 05 |
| Sodium starch glycolate | 4 |
| Povidone | 4 |
| Purified water | Q.s |
| Magnesium stearate | 1 |
| Colloidal silicon dioxide | 1 |
| Total | 100 |

Procedure: Extracts of *Curcuma longa, Phyllanthus emblica, Gymnosporia montana*, lactose anhydrous and sodium starch glycolate are shifted through 40#. All the shifted materials are mixed for 5 minutes. The mixed materials are granulated with binder solution of povidone prepared in purified water. The granules are dried and shifted through 20#. Dried granules are mixed with magnesium stearate and colloidal silicon dioxide which are shifted through 40#. The lubricated granules are compressed using appropriated punch tolling.

Example 3

Comparison: plant extracts composition of the present invention with conventional treatment against liver dysfunction condition.

Total 8 patients with liver dysfunction condition were involved in the trial and were given conventional allopathic treatment for 6 days and the treatment with the plant extract composition of the present invention (HIPATONE™ as per example 1) three times a day and after both the treatment, patients were evaluated based on the pathological parameters and the results are mentioned in Table 1.

Parameters evaluated are total bilirubin, SGPT, urine bile salts and urine bile pigments.

The result shows significant improvement in the condition of patient after plant extracts composition (HIPATONE™ treatment) compared to conventional treatment.

Individual extracts of all three had been also clinically observed but has no significant effects against "HIPATONE™" composition. The human subjects observed for each individual compound were twelve in numbers. The dosage regimes were two capsule three times a day for each individual compound for eight days.

TABLE 1

Results after conventional and HIPATONE ™ treatment
Normal: Direct: 0.2-1.0 - Indirect: 0.0-0.8 -S.G.P.T: 0.45
Urine Bile Salts: Absent- Urine bile Pigments: Absent

| Patient Code | Age | Treatment (for 6 days) | Total Bilirubin (mg/dl) | S.G.P.T (u/L) | Urine Bile Salts | Urine Bile Pigments |
|---|---|---|---|---|---|---|
| DP | 43 | Conventional Treatment | 10.03 | 265 | Present | Present |
|  |  | HIPATONE Treatment | 0.9 | 0.6 | Absent | Absent |
| NJ | 44 | Conventional Treatment | 9.07 | 325 | Present | Present |
|  |  | HIPATONE Treatment | 0.7 | 0.45 | Absent | Absent |
| CS | 19 | Conventional Treatment | 9.17 | 492 | Present | Present |
|  |  | HIPATONE Treatment | 0.5 | 44 | Absent | Absent |
| RP | 37 | Conventional Treatment | 8.87 | 187 | Absent | Present |
|  |  | HIPATONE Treatment | 0.45 | 45 | Absent | Absent |
| KP | 27 | Conventional Treatment | 7.24 | 187 | Present | Present |

TABLE 1-continued

Results after conventional and HIPATONE ™ treatment
Normal: Direct: 0.2-1.0 - Indirect: 0.0-0.8 -S.G.P.T: 0.45
Urine Bile Salts: Absent- Urine bile Pigments: Absent

| Patient Code | Age | Treatment (for 6 days) | Total Bilirubin (mg/dl) | S.G.P.T (u/L) | Urine Bile Salts | Urine Bile Pigments |
|---|---|---|---|---|---|---|
| | | HIPATONE Treatment | 0.3 | 46 | Absent | Absent |
| AD | 32 | Conventional Treatment | 5.03 | 97 | Present | Present |
| | | HIPATONE Treatment | 0.4 | 44 | Absent | Absent |
| VG | 48 | Conventional Treatment | 9.87 | 324 | Present | Present |
| | | HIPATONE Treatment | 2.04 | 123 | Absent | Absent |
| RA | 18 | Conventional Treatment | 4.35 | 127 | Present | Present |
| | | HIPATONE Treatment | 0.46 | 45 | Absent | Absent |
| HR | 23 | Conventional Treatment | 5.94 | 146 | Present | Present |
| | | HIPATONE | 0.43 | 44 | Absent | Absent |
| JA | 48 | Conventional Treatment | 3.78 | 137 | Present | Present |
| | | HIPATONE | 0.46 | 47 | Absent | Absent |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A plant extracts composition for treatment of liver dysfunction wherein said composition comprises 10-25% w/w extract of *Curcuma longa*, 10-25% w/w extract of *Phyllanthus emblica*, 50-70% w/w extract of *Gymnosporia Montana* and at least one carrier.

2. The plant extracts composition according to claim 1, wherein said extract of *Curcuma longa* is prepared from tubers of *Curcuma longa*.

3. The plant extracts composition according to claim 1, wherein said extract of *Phyllanthus emblica* is prepared from fruits of *Phyllanthus emblica*.

4. The plant extracts composition according to claim 1, wherein said extract of *Gymnosporia montana* is prepared from leaves of *Gymnosporia montana*.

5. The plant extract composition according to claim 1, wherein said composition is in a form selected from a group consisting of tablet, capsule, powder, beads, pellets, granules, solution, syrup, suspension, emulsion or injection.

6. The plant extracts composition according to claim 1, wherein said carrier is selected from a group consisting of diluent, binder, disintegrant, glidant and lubricant.

7. A method of preparing the plant extracts composition as claimed in claim 1, wherein said method comprising the steps of:
   a) sifting the extracts of *Curcuma longa, Phyllanthus emblica, Gymnosporia montana* through #20 screen and at least one carrier through #40 screen and;
   b) mixing of sifted extracts of step a);
   c) granulating the material of step b) using solvent;
   d) drying of granules of step c);
   e) sifting dried granules of step d) through #20 screen and
   f) mixing materials of step b) or e) with at least a carrier from step a) and
   g) filling of material of step f) into capsules or compressing in to tablets.

8. A method for treatment of conditions of liver dysfunction in a subject, said method comprising administering a therapeutically effective amount of the composition of claim 1 to the subject in need thereof.

9. A method for treatment of Jaundice and Hepatic insufficiency in a subject, said method comprising administering a therapeutically effective amount of the composition of claim 1 to the subject in need thereof.

* * * * *